United States Patent [19]
Prabhu

[11] Patent Number: 5,955,633
[45] Date of Patent: Sep. 21, 1999

[54] SYNTHESIS OF TERTIARY AMINE OXIDES

[75] Inventor: Vaikunth S. Prabhu, Morgantown, W. Va.

[73] Assignee: General Electric Company, Pittsfield, Mass.

[21] Appl. No.: 09/137,172

[22] Filed: Aug. 20, 1998

Related U.S. Application Data

[62] Division of application No. 08/820,871, Mar. 20, 1997, Pat. No. 5,866,718.

[51] Int. Cl.$^6$ ................................................ C07C 213/00
[52] U.S. Cl. .............................................................. 564/298
[58] Field of Search ............................................. 564/298

[56] References Cited

U.S. PATENT DOCUMENTS

| | | |
|---|---|---|
| 2,497,061 | 2/1950 | Kellog . |
| 2,586,236 | 2/1952 | Lewis et al. . |
| 2,586,238 | 2/1952 | Lytton . |
| 3,047,579 | 7/1962 | Witman . |
| 3,098,794 | 7/1963 | Dohr et al. . |
| 3,249,587 | 5/1966 | Searles, Jr. . |
| 3,309,399 | 3/1967 | Zienty et al. . |
| 3,408,422 | 10/1968 | May . |
| 3,412,155 | 11/1968 | Miller, Jr. et al. . |
| 3,432,578 | 3/1969 | Martin . |
| 3,468,869 | 9/1969 | Sherburne . |
| 3,501,426 | 3/1970 | Yu . |
| 3,576,877 | 4/1971 | Albert et al. . |
| 3,644,244 | 2/1972 | Fryd et al. . |
| 3,644,278 | 2/1972 | Klemchuk . |
| 3,776,959 | 12/1973 | Stalioraitis et al. . |
| 3,778,464 | 12/1973 | Klemchuk . |
| 3,926,909 | 12/1975 | Wei . |
| 3,957,873 | 5/1976 | Thigpen et al. . |
| 4,136,039 | 1/1979 | Jager et al. . |
| 4,247,480 | 1/1981 | Murata et al. . |
| 4,263,177 | 4/1981 | Egan et al. . |
| 4,305,866 | 12/1981 | York et al. . |
| 4,316,996 | 2/1982 | Collonge et al. . |
| 4,386,224 | 5/1983 | Deetman . |
| 4,395,373 | 7/1983 | Login et al. . |
| 4,403,053 | 9/1983 | Lewis . |
| 4,416,808 | 11/1983 | Blaschke et al. . |
| 4,443,572 | 4/1984 | Burns . |
| 4,504,666 | 3/1985 | Earl et al. . |
| 4,565,891 | 1/1986 | Correa et al. . |
| 4,590,231 | 5/1986 | Seltzer et al. . |
| 4,612,393 | 9/1986 | Ravichandran et al. . |
| 4,649,221 | 3/1987 | Ravichandran et al. . |
| 4,650,904 | 3/1987 | Fujita . |
| 4,659,565 | 4/1987 | Smith et al. . |
| 4,668,721 | 5/1987 | Seltzer et al. . |
| 4,696,964 | 9/1987 | Ravichandran . |
| 4,748,275 | 5/1988 | Smith et al. . |
| 4,782,105 | 11/1988 | Ravichandran et al. . |
| 4,826,506 | 5/1989 | Vardi et al. . |
| 4,876,300 | 10/1989 | Seltzer et al. . |
| 4,889,954 | 12/1989 | Laurenzo et al. . |
| 4,942,260 | 7/1990 | Laurenzo et al. . |
| 4,960,934 | 10/1990 | Smith et al. . |
| 4,970,340 | 11/1990 | Smith . |
| 4,970,341 | 11/1990 | Summerford . |
| 4,994,614 | 2/1991 | Bauer et al. . |
| 5,055,614 | 10/1991 | Sauer et al. . |
| 5,059,625 | 10/1991 | Scardera et al. . |
| 5,068,430 | 11/1991 | Borland et al. . |
| 5,120,469 | 6/1992 | Smith et al. . |
| 5,130,488 | 7/1992 | Smith et al. . |
| 5,134,183 | 7/1992 | Odorisio et al. . |
| 5,149,774 | 9/1992 | Patel et al. . |
| 5,166,435 | 11/1992 | Sharma et al. . |
| 5,208,374 | 5/1993 | Borland et al. . |
| 5,219,910 | 6/1993 | Stahl et al. . |
| 5,223,644 | 6/1993 | Blezard et al. . |
| 5,254,735 | 10/1993 | Smith et al. . |
| 5,268,114 | 12/1993 | Odorisio et al. . |
| 5,292,954 | 3/1994 | Borland et al. . |
| 5,389,306 | 2/1995 | Wierenga et al. . |
| 5,409,532 | 4/1995 | Astegger et al. . |
| 5,442,113 | 8/1995 | Blezard et al. . |
| 5,466,870 | 11/1995 | Miller et al. . |
| 5,498,373 | 3/1996 | Miller et al. . |
| 5,503,749 | 4/1996 | Manner et al. . |
| 5,543,515 | 8/1996 | Koehler et al. . |
| 5,583,258 | 12/1996 | Hawkins . |

FOREIGN PATENT DOCUMENTS

| 0 470 048 A2 | 2/1992 | European Pat. Off. . |
|---|---|---|

OTHER PUBLICATIONS

Organicreations, Chapter 5—by A. Cope and E. Trumbull, 1964.
Amine Oxides—by Richard J. Nadolsky, 1975.

*Primary Examiner*—James H. Reamer

[57] ABSTRACT

A process is provided for the manufacture of free-flowing solid tertiary amine oxides having N-nitrosodimethylamine levels of less than about 250 ppb. The process comprises heating a mixture of a tertiary amine, a polar hydroxy alkyl solvent, an organic acid, and aqueous hydrogen peroxide, followed by removal of the solvent and water, preferably by azeotropic removal. The resultant tertiary amine oxides have good color without bleaching and are useful without further purification.

22 Claims, No Drawings

SYNTHESIS OF TERTIARY AMINE OXIDES

This is a divisional of application Ser. No. 08/820,871 filed on Mar. 20, 1997, now U.S. Pat. No. 5,866,718.

FIELD OF THE INVENTION

The present invention relates to a process for the manufacture of free-flowing solid tertiary amine oxides having nitrosamine levels of less than 100 ppb. The process comprises heating a mixture of a tertiary amine, a polar hydroxy alkyl solvent, an organic acid, and aqueous hydrogen peroxide, followed by azeotropic removal of the solvent and water. The resultant solid tertiary amine oxides have good color without bleaching and are useful without further purification.

BACKGROUND OF THE INVENTION

Tertiary amine oxides are widely used commercially as organic surfactants. Such surfactants have properties that make them very useful in shampoos, hair conditioners, dish and laundry detergents, fabric softeners and the like. In these applications, the tertiary amine oxides are employed as aqueous solutions. More recently, however, there has been interest in the use of tertiary amine oxides as additives for thermoplastic resins. In these new additive applications it is important to have a high solids level, preferably a solid tertiary amine oxide containing a minimal amount of volatile solvents to avoid difficulties in removing the solvent during the compounding and processing operations.

Nitrosamines have been reported as minor by-products in the conventional preparation of tertiary amine oxides using aqueous hydrogen peroxide. Although the amount of nitrosamine is very small, on the order of only a few hundred parts per billion (ppb), this small amount renders the amine oxide unsuitable in many applications that involve human contact. This is because nitrosamines are reported to be carcinogenic and/or mutagenic. Hence, a need exists for a method for making tertiary amine oxides in high conversion and yield and at a fast reaction rate while at the same time producing tertiary amine oxide products that are solids at ambient temperatures and that are substantially free of nitrosamines (i.e. have a level of N-nitrosodimethyl amine of less that about 100 ppb). The present invention provides such a process.

BACKGROUND ART

Tertiary amine oxides are generally reported to be made by the reaction of an appropriate tertiary amine with aqueous hydrogen peroxide. Such processes are reported in U.S. Pat. No. 4,748,275 (Smith et al.) and the references discussed therein. The reaction is typically conducted at 50°–75° C. and requires a long reaction period to obtain complete conversion of the amine.

Promoters have been reported to increase the rate and degree of the conversion. Carbon dioxide appears to be a preferred example as reported in the processes of U.S. Pat. No. 4,247,480 (Murata et al.). These aqueous processes are quite satisfactory for the products which are to be used in applications in which their water content can be tolerated.

The oxidation of tertiary amines has also been reported in organic solvents, such as in U.S. Pat. Nos. 3,776,959 (Stalioraitis et al.); 4,659,565 (Smith et al.); 4,748,275 (Smith et al.); and 5,130,488 (Smith et al.). These processes are also very satisfactory for some purposes, however, the products formed either are oily in nature or the processes have undesirable limitations on the ratios of water to solvent that can be utilized. For example, the process described in U.S. Pat. No. 5,130,488 (Smith et al.) limits the ratio of water to organic solvent to 2.1/1 in order to be able to recover the amine oxide from the reaction mixture.

It has now been discovered that solid tertiary amine oxides that are substantially free from nitrosamines (i.e. have a level of N-nitrosodimethyl amine of less that about 100 ppb) can be produced in high yield and at a fast reaction rate by reacting an appropriate tertiary amine in a polar hydroxy alkyl solvent with an organic acid and aqueous hydrogen peroxide, followed by azeotropic removal of the solvent and water. The resultant tertiary amine oxides are free-flowing solids having good color without bleaching and are useful without further purification.

DETAILED DESCRIPTION OF THE INVENTION

A preferred embodiment of the invention is a process for making a substantially nitrosamine-free amine oxide that is a free-flowing solid at ambient temperature (i.e. 23° C.) by reacting a tertiary amine capable of forming an amine oxide in a polar hydroxy alkyl solvent at about 50°–100° C. with a promoter and aqueous hydrogen peroxide, followed by azeotropic removal of the solvent, organic acid, and water. By free-flowing solid is meant a solid material that does not agglomerate (i.e. stick together) in a particulate form and/or does not adhere to other surfaces. A free-flowing solid may be characterized as readily transferable between containers without appreciable loss of the solid due to adherence to the first container.

In another preferred embodiment, the present process affords a tertiary amine oxide of the general formula

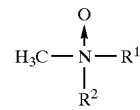

wherein $R^1$ and $R^2$ are each independently a $C_{8-30}$ alkyl moiety.

In another preferred embodiment, the present process affords a tertiary amine oxide of the general formula

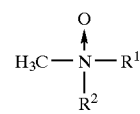

wherein $R^1$ and $R^2$ are each independently a $C_{16-18}$ alkyl moiety; and wherein the amine oxide picks up less than about 10% by weight water when stored at 23° C. and 80% relative humidity, and is a solid at 23° C.

In another preferred embodiment, the present process affords a tertiary amine oxide of the general formula

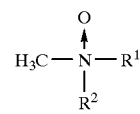

wherein $R^1$ and $R^2$ are each independently a $C_{20-22}$ alkyl moiety; and wherein the amine oxide picks up less than about 5% by weight water when stored at 23° C. and 80% relative humidity, and is a solid at 23° C.

In another preferred embodiment, the present process affords a tertiary amine oxide of the general formula

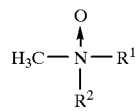

wherein $R^1$ and $R^2$ are each independently a $C_{10}$ alkyl moiety; and wherein the amine oxide has a 10% weight loss rating of at least about 120° C., when measured at a heating rate of 20° C./minute.

In another preferred embodiment, the present process affords a tertiary amine oxide of the general formula

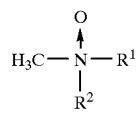

wherein $R^1$ and $R^2$ are each independently a $C_{16-18}$ alkyl moiety; and wherein the amine oxide has a 10% weight loss rating of at least about 145° C., when measured at a heating rate of 20° C./minute.

In another preferred embodiment, the present process affords a tertiary amine oxide of the general formula

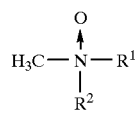

wherein $R^1$ and $R^2$ are each independently a $C_{20-22}$ alkyl moiety; and wherein the amine oxide has a 10% weight loss rating of at least about 220° C., when measured at a heating rate of 20° C./minute.

In general, the process of the present invention is applicable to any tertiary amine capable of forming an amine oxide. However, in order to obtain a tertiary amine oxide that is a solid at room temperature, the tertiary amine should have the general formula

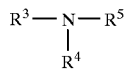

wherein $R^3$ is a $C_{1-30}$ alkyl moiety and $R^4$ and $R^5$ are each independently a $C_{8-30}$ alkyl moiety. For use as thermoplastic additives, it is preferred that $R^3$ is a methyl group and $R^4$ and $R^5$ are each independently a $C_{8-30}$. At least one R group may, however, optionally contain at least one —O—, —S—, —SO—, —CO$_2$—, —CO—, or —CON— moiety. In another embodiment of the present invention, the tertiary amine may be a poly(tertiary amine). By poly(tertiary amine) is meant a compound or resin containing on average more than one tertiary amine. Illustrative poly(tertiary amines) include the tertiary amine analogues of aliphatic and alicyclic diamines such as, for example, 1,4-diaminobutane; 1,6-diaminohexane; 1,10-diaminodecane; and 1,4diaminocyclohexane, and aromatic based diamines such as, for example, diamino anthraquinones and diaminoanisoles. Also included are tertiary amines derived from oligomers and polymers of diamines.

Useful tertiary amines also include tertiary amines attached to polymers, for example, polyolefins, polyacrylates, polyesters, polyamides, polystyrenes, and the like. When the tertiary amine is attached to a polymer, the average number of tertiary amines per polymer can vary widely as not all polymer chains need to contain a tertiary amine. Generally a useful number of tertiary amine moieties in the overall polymer is between about 0.001 weight percent and about 5 weight percent, based on the weight of the polymer. All of the aforementioned tertiary amines may optionally contain at least one —O—, —S—, —SO—, —CO$_2$—, —CO—, or —CON— moiety.

Especially preferred tertiary amines, due in part to their wide commercial availability in high purity and relatively low cost; include didecyl methyl amine (i.e. $R^4$ and $R^5$ are each primarily a $C_{10}$), dicoco methyl amine (i.e. $R^4$ and $R^5$ are each primarily a $C_{12-16}$), ditallow methyl amine (i.e. $R^4$ and $R^5$ are each primarily a $C_{16-18}$), dieicosyl methyl amine (i.e. $R^4$ and $R^5$ are each primarily a $C_{20}$), and didocosanyl methyl amine (i.e. $R^4$ and $R^5$ are each primarily a $C_{22}$), as well as mixtures of tertiary amines containing at least one of the aforementioned amines. It should be noted that these tertiary amines are commercially available generally as at least 80% enriched with the aforementioned alkyl groups, however, other alkyl amine fractions are present in the tertiary amines. Although higher purity of a single tertiary amine may be desirable for some applications, the cost to produce extremely high purity tertiary amines may be prohibitive.

As previously mentioned, it is an object of the present invention to provide a simple and economic process for preparing tertiary amine oxides that are free-flowing solids at ambient temperature and that have a low nitrosamine content. In order to accomplish this objective, the tertiary amine used as the starting material should have a total content of primary and secondary amines of not more than about 1% by weight, preferably less than about 0.5% by weight.

These tertiary amines may be obtained by distillation from the relevant tertiary amines that have the undesired primary and/or secondary amines present from the preparation of the tertiary amine. Alternatively, scavengers which selectively react with the primary and secondary amines may also be added to reduce the level of primary and secondary amines. The scavengers which can be used for this purpose are in principle substances which react faster with primary and secondary amines than with tertiary amines and whose reaction with these amines takes place as completely as possible after a short time.

Useful scavengers include those found in U.S. Pat. No. 5,543,515. Illustrative scavengers include the following classes of compounds: haloformates, haloformamides, carboxylic anhydrides, acyl halides, carboxylic esters, ketenes and their dimers, phosgene, carbonic esters, pyrocarbonic esters, isocyanates, phosphinyl halides, phosphonyl halides, phosphoryl halides, sulfenyl halides, sulfonyl halides, sulfonic esters and anhydrides. The compounds formed can remain in the tertiary amine treated without interfering with the subsequent generation of the tertiary amine oxide with a peroxide, in particular hydrogen peroxide. However, it is preferable to remove the scavengers and their derivatives which are formed on reaction with the primary and/or secondary amines from the tertiary amine by distillation, extraction, filtration, and/or centrifugation.

Any aqueous hydrogen peroxide can be used including those containing 3–100 percent hydrogen peroxide. Preferably the hydrogen peroxide is between about 20–70 weight percent, more preferably between 45–70 weight percent active hydrogen peroxide. Due to the presence of the solvent in the present process, more concentrated hydrogen peroxide can be used without presenting difficulties in stirring the reaction mixture.

A useful amount of hydrogen peroxide should be at least a stoichiometric amount. The range is typically between about 1–5 moles of hydrogen peroxide, more preferably 1–1.5 mole of hydrogen peroxide, per mole of tertiary amine. A highly preferred amount is about 1.05–1.3 moles of hydrogen peroxide, and especially about 1.1–1.2 moles, of hydrogen peroxide per mole of tertiary amine. Any excess hydrogen peroxide remaining after the reaction can be destroyed by the addition of a reducing agent, for example, sodium sulfite, sodium thiosulfate, and/or sodium thiosulfite. Peroxide decomposition catalysts such as, for example, those based on platinum or manganese are also useful. Additionally, enzymes known in the art such as those available from Novo Nordisk under the tradename Catazyme, including product 50L, have been shown to be efficient for destroying any excess hydrogen peroxide remaining.

The organic solvent used in the present invention may be any organic liquid in which the tertiary amine and tertiary amine oxide are soluble at the reaction temperature and which is capable of forming an azeotrope with water. However, to avoid the danger of explosion, this solvent should be substantially inert. In a preferred embodiment of the invention, the solvent is capable of maintaining the reaction mixture fluid and stirrable without being used in an amount that would reduce the solids content of the reaction mixture below about 15% by weight, preferably below about 30% by weight. Excellent results have been achieved at a solids level of about 50% by weight.

Based on cost and availability, as well as effectiveness, the preferred solvents for use in the process are the lower alkyl alcohols, such as the $C_{1-8}$ alcohols, and especially the $C_{1-4}$ alcohols, containing one or more hydroxyl groups. Exemplary alcohols include methanol, ethanol, 1-propanol, 2-propanol, 1-butanol, 2-butanol, 1-pentanol, 2-pentanol, 3-pentanol, tert-butyl alcohol, 1-hexanol, 2-hexanol, 3-hexanol, 2-methyl-1-propanol, 2-methyl-2-propanol, tert-amyl alcohol, 2-methyl-1-butanol, 3-methyl-1-butanol, 3-methyl-2-butanol, neopentyl alcohol, 2,3-dimethyl-2-butanol, 3,3-dimethyl-2-butanol, 1-hexyl alcohol, 2-hexanol, 3-hexanol, and the like as well as various mixtures thereof. Especially preferred solvents include 1-propyl alcohol, 2-propyl alcohol, 1-butanol, and 2-butanol.

The solvent may optionally contain another solvent such as an aliphatic, cycloaliphatic, or aromatic hydrocarbon such as hexane, isohexane, heptane, 2-ethylhexane, octane, isooctane, cyclohexane, cyclooctane, toluene, or the like, or a halohydrocarbon such as chlorobenzene, dichlorobenzene, bromobenzene, chlorotoluene, 2,4-dichlorotoluene, and the like. Ester solvents are also useful as a co-solvent and exemplary ester solvents include methyl acetate, ethyl acetate, isopropyl acetate, butyl acetate, sec-butyl acetate, t-butyl acetate, isobutyl acetate, amyl acetate, and the corresponding propionates, butyrates, and valerates. When the optional co-solvent is used, the amount is generally limited to an amount up to about 25% (e.g., 1–25%) by weight based on the weight of the polar solvent. The use of the non-polar solvent reduces the solubility of the tertiary amine and/or amine oxide in the reaction mixture.

The present process also includes the use of a promoter for the oxidation of the tertiary amine. Preferred promoters include lower organic acids that are capable of removal by distillation from the reaction mixture at the completion of the oxidation. Preferred acids include: formic acid, acetic acid, and propionic acid with acetic acid being especially preferred. Other organic carboxylic acids, such as diethylenetriaminepentaacetic acid or ethylenediaminetetracarboxylic acid, are also useful. Other promoters include ammonium carbonate, ammonium bicarbonate, and ammonium carbamate, as well as mixtures of promoters. Carbon dioxide and aluminum are also an effective promoters.

The amount of promoter can vary over a wide range. It is required that the amount of promoter in the reaction mixture, in whatever form it exists, be an amount which causes the reaction to proceed at a faster rate than the rate achieved without the addition of the promoter. In other words there should be at least a catalytic amount of the promoter. Useful concentrations of the promoter include from about 0.001–10 weight percent based on weight of the tertiary amine. A preferred concentration is about 0.005–1 weight percent. A more preferred concentration is about 0.01–0.8 weight percent. When carbon dioxide is added as a promoter, it may be added as a blanket over the reaction mixture, or more preferably, the carbon dioxide can be dissolved in the aqueous hydrogen peroxide and/or in the solvent.

The reaction can be conducted over a wide temperature range. The temperature should be high enough to cause the reaction to proceed at a reasonable rate but not so high as to lead to decomposition of the reactants or products. A useful temperature range is from about 0°–140° C. A more preferred temperature range is about 40°–140° C. A still more preferred temperature range is about 45°–130° C. Most preferably the reaction is conducted at about 45°–110° C. In this temperature range the reaction is quite rapid and is normally complete in less than about 30 hours, generally less than about 20 hours. Excellent results have been achieved at about 55°–90° C.

The process of the invention is conducted by adding the aqueous hydrogen peroxide to a solution of the tertiary amine in the solvent containing the promoter. The organic solvent is generally present throughout the reaction, although the amount present at any point during the reaction is quite flexible. The organic solvent may be minimized during initiation of the reaction and then gradually added during the course of the reaction to maintain the reaction mixture fluid and stirrable. Alternatively, the organic solvent may be entirely added at the beginning of the reaction or may be added later during the course of the reaction provided that the solvent is present for the azeotropic removal of the water from the aqueous hydrogen peroxide. The hydrogen peroxide is preferably added at a controlled rate such that the temperature is preferably maintained within the ranges as previously discussed. Cooling may become necessary to maintain the temperature within the desired range. The addition rate of the hydrogen peroxide is, preferably, such that a large accumulation of unreacted hydrogen peroxide is not present at any particular moment in time. The reaction temperature is maintained within the temperature range until the oxidation is substantially complete, generally in less than about fifty hours, generally less than about forty hours.

When the reaction has been completed, the amine oxide may be recovered immediately by removing the organic solvent and water as an azeotrope. Alternatively, the azeotropic mixture may be removed during the course of the reaction with additional solvent added to the reaction. The azeotropic mixture is preferably removed with the aid of a vacuum, typically of at least 25 mm of mercury, with sufficient organic solvent added to insure complete removal of the water from the hydrogen peroxide. The tertiary amine oxide is thus recovered as a solid in either the dihydrate, the monohydrate, and/or the anhydrous form.

The recovered amine oxide may be utilized as collected or the purity of the amine oxide may be improved by recrystallizing it one or more times from an organic solvent in which it can be dissolved at a higher temperature and from which it can be precipitated at a lower temperature.

Recrystallization can also be used to reduce the water content of the recovered amine oxide, if desired, by using an organic solvent, such as ethyl acetate, in which water is at least partially soluble. For example, if the amine oxide is recovered as a dihydrate, and it is wished to convert it to an oxide containing a lesser amount of water, e.g., to a mixture of dihydrate, monohydrate, and anhydrous oxide or to the monohydrate or anhydrous form, the amine oxide can be recrystallized from such an organic solvent until the desired degree of dehydration is accomplished.

The invention is advantageous as a means of preparing free-flowing solid tertiary amine oxides that can be used in the preparation of powdered compositions, such as dry polymer additive mixtures, without first being subjected to after-treatments that could increase their cost and/or contaminate them with materials used in the after-treatments or decomposition products formed during the after-treatments.

The amine oxides formed by the process can all be regarded as solids, although the lower molecular weight ones have melting points that put them at the borderline between solids and liquids at some use temperatures; and the amine oxides that are recovered as dihydrates have the additional advantage of being substantially non-hygroscopic or having a low hygroscopic character. By low hygroscopic character is meant that the tertiary amine oxide has a water pick-up of about 10% by less by weight after a twenty-four hour exposure to 80% relative humidity at 23° C. The preferred tertiary amine oxides of the present invention will remain a solid at room temperature (i.e. 23° C.) even with a water absorption level of about 10% by weight. These products, whether they are dihydrates, amine oxides which are less than 100% dihydrate, monohydrates, or anhydrous amine oxides, have general utility in the same applications as the mixed tert-amine oxides prepared by conventional techniques, although their primary attractiveness is their having a form that makes them so well suited for incorporation into dry formulations.

It should be clear that the present invention affords a process for producing anhydrous amine oxides wherein said process comprises reacting a tertiary amine of the formula

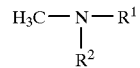

wherein $R^1$ and $R^2$ are each independently a $C_{8-30}$ alkyl moiety, with aqueous hydrogen peroxide and an amount of an organic carboxylic acid effective to catalyze the oxidation of the tertiary amine to produce a tertiary amine oxide, wherein said reaction is done in a polar hydroxy alkyl solvent; wherein said solvent can form an azeotrope of at least one percent by weight water; and isolating the tertiary amine oxide by removal of the solvent. It should also be clear that at least one of the aforementioned R groups may optionally contain at least one —O—, —S—, —SO—, —CO$_2$—, —CO—, or —CON— moiety.

More specifically, it should be clear that the present invention affords a process for making solid tertiary amine oxides, said process comprising heating under a nitrogen atmosphere a tertiary amine, iso-propyl alcohol, acetic acid, and aqueous hydrogen peroxide to a temperature between about 50° C. and about 100° C. until at least about 95% of the tertiary amine oxide has reacted, and removing the iso-propyl alcohol and water, preferably as an azeotrope, to yield a free-flowing solid tertiary amine oxide.

In a preferred embodiment of the present invention includes a process to make an amine oxide of the formula

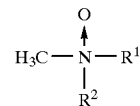

wherein $R^1$ and $R^2$ are each a $C_{10}$ alkyl moiety; and wherein the amine oxide has a 10% weight loss rating of at least about 120° C., when measured at a heating rate of 20° C./minute. In another preferred embodiment of the present invention includes a process to make an amine oxide of the formula

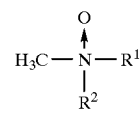

wherein $R^1$ and $R^2$ are each $C_{16-18}$ alkyl moieties; and wherein the amine oxide picks up less than about 10% by weight water when stored at 23° C. and 80% relative humidity, and remains a solid at 23° C. In yet another preferred embodiment of the present invention includes a process to make an amine oxide of the formula

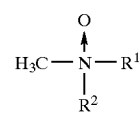

wherein $R^1$ and $R^2$ are each $C_{20-22}$ alkyl moieties; and wherein the amine oxide picks up less than about 5% by weight water when stored at 23° C. and 80% relative humidity, and remains a solid at 23° C.

All patents cited by reference are incorporated by reference herein.

In order that those skilled in the art will be better able to practice the invention, the following examples are given by way of illustration and not by way of limitation.

EXAMPLES

Example 1

A reaction vessel is charged with 62.2 g (0.2 mol) of didecylmethylamine and 0.3 g of acetic acid in 62.2 g of 2-propanol. The mixture is heated, with stirring, to about 50°–55° C., followed by addition of 16.32 g (0.24 mol) of 50% aqueous hydrogen peroxide dropwise over about a 60-minute period. The temperature is increased to 60°–65° C., and the reaction mixture was stirred at that temperature for about 18 hours. Proton NMR analysis shows 99+% conversion of the amine (i.e. the level of unreacted tertiary amine was undetectable). The product was recovered by removal of the solvent azeotrope at about 40°–50° C. under a vacuum of about 15–20 mm of mercury, followed by increasing the vacuum to about 1 mm of mercury and increasing the temperature to about 65°–70° C. for about 1 to 4 hours. Analysis showed the product to be anhydrous N,N-didecyl-N-methylamine oxide, a solid having a melting point of about 40°–45° C. The level of N-nitrosodimethylamine was measured as less than 93 ppb. The recovered yield was 61.44 g (93.3%) as a free-flowing white solid.

Using the process described in Example 1, a variety of tertiary amine oxides have been produced. Analysis of some of these illustrative tertiary amine oxides is found in Table 1.

TABLE 1

| Tertiary amine: | $(C_4H_9)_3N$ | $(CH_3)N(C_{10}H_{21})_2$ | $(CH_3)N(C_{16-18}H_{33-37})_2$ | $(CH_3)N(C_{20-22}H_{41-45})_2$ |
|---|---|---|---|---|
| yield | n.a. | 93.3 | >90 | >90 |
| N-nitrosodimethyl amine, ppb[1] | n.a. | <100 | <100 | n.a. |
| melting point | liquid | 40–45 | 80–88 | 95–102 |
| Water pick-up[2] | | | | |
| 24 h | very hygroscopic | 10.02 (solid) | 2.05 (solid) | 0.9815 (solid) |
| 120 h | | 19.76 (liquid) | 4.46 (solid) | 1.2805 (solid) |
| 953 h | | 20.88 (liquid) | 5.08 (solid) | 1.4001 (solid) |
| Percent wt. Loss (10%)[3] | — | 127 | 157 | 228 |
| Color | colorless liquid | white/colorless | white/colorless | white/colorless |

[1]The lowest detection limit was 100 ppb.
[2]Water pick-up was measured at 80% relative humidity and 23° C.
[3]Measured with a universal V1-5B TA Instruments TGA utilizing a 50 mL/min nitrogen purge and a temperature range of 20°–500° C. at a rate of 20° C./min.

These results illustrate that free-flowing solid tertiary amine oxides can be prepared by the process of the present invention. The solid tertiary amine oxides have N-nitrosodimethylamine levels of less than 100 ppb and are obtained in high yields. The amine oxides are useful without additional purification.

What is claimed:

1. A process for producing amine oxides, wherein said process comprises reacting a tertiary amine of the formula

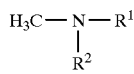

wherein $R^1$ and $R^2$ are each independently a $C_{8-30}$ alkyl moiety, with aqueous hydrogen peroxide and an amount of an organic carboxylic acid effective to catalyze the oxidation of the tertiary amine to produce a tertiary amine oxide, wherein said reaction is done in at least one polar hydroxy alkyl solvent;

wherein said solvent can form an azeotrope of at least one percent by weight water;

and isolating the tertiary amine oxide by removal of said solvent.

2. The process of claim 1, wherein the amine oxide after isolation is a solid at 23° C.

3. The process of claim 1, wherein the amine oxide after isolation contains less that about 100 ppb of N-nitrosodimethylamine.

4. The process of claim 1, where in the solvent is removed with a vaccum.

5. The process of claim 1, wherein the amine oxide has the formula

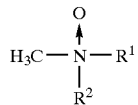

wherein $R^1$ and $R^2$ are each $C_{16-18}$ alkyl moieties; and wherein the amine oxide picks up less than about 10% by weight water when stored at 23° C. and 80% relative humidity, and remains a solid at 23° C.

6. The process of claim 1, wherein the amine oxide has the formula

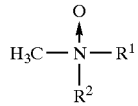

wherein $R^1$ and $R^2$ are each $C_{20-22}$ alkyl moieties; and wherein the amine oxide picks up less than about 5% by weight water when stored at 23° C. and 80% relative humidity, and remains a solid at 23° C.

7. The process of claim 1, wherein the amine oxide has the formula

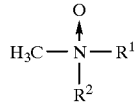

wherein $R^1$ and $R^2$ are each a $C_{10}$ alkyl moiety; and wherein the amine oxide has a 10% weight loss rating of at least about 120° C., when measured at a heating rate of 20° C./minute.

8. The process of claim 1, wherein the amine oxide has the formula

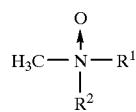

wherein $R^1$ and $R^2$ are each a $C_{16-18}$ alkyl moiety; and wherein the amine oxide has a 10% weight loss rating of at least about 145° C., when measured at a heating rate of 20° C./minute.

9. The process of claim 1, wherein the amine oxide has the formula

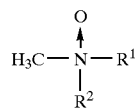

wherein $R^1$ and $R^2$ are each a $C_{20-22}$ alkyl moiety; and wherein the amine oxide has a 10% weight loss rating of at least about 220° C., when measured at a heating rate of 20° C./minute.

10. The process of claim 1, wherein the polar hydroxy alkyl solvent is selected from the group consisting of $C_{1-8}$ alcohols containing one or more hydroxyl groups.

11. A process for making solid tertiary amine oxides, said process comprising heating under a nitrogen atmosphere a tertiary amine, an polar hydroxy alkyl solvent, an organic acid, and aqueous hydrogen peroxide to a temperature between about 50° C. and about 100° C. until at least about 95% of the tertiary amine oxide has reacted and removing the polar hydroxy alkyl solvent, the organic acid, and water as an azeotrope to yield a free-flowing solid tertiary amine oxide.

12. The process of claim 11, wherein the solid tertiary amine oxide comprises at least 90% tertiary amine oxide.

13. The process of claim 11, wherein the polar hydroxy alkyl solvent is selected from the group consisting of $C_{1-8}$ alcohols containing one or more hydroxyl groups.

14. The process of claim 11, wherein the organic acid is at least one acid selected from the group consisting of acetic acid, formic acid, and propionic acid.

15. The process of claim 11, wherein the aqueous hydrogen peroxide contains between about 20% to 90% by weight hydrogen peroxide.

16. The process of claim 11, wherein the molar ratio of the tertiary amine to hydrogen peroxide is between about 1:1 to about 1:2.

17. The process of claim 11, wherein said process produces less than about 250 parts per billion of a nitrosamine based upon the weight of the tertiary amine oxide.

18. The process of claim 11, wherein the weight ratio of the tertiary amine to the organic acid is between about 50:1 to about 500:1.

19. The process of claim 11, wherein the tertiary amine is at least one amine of the formula:

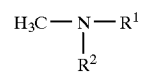

wherein $R^1$ and $R^2$ are each independently a $C_{1-30}$ alkyl moiety, and wherein at least one of $R^1$ and $R^2$ may optionally contain at least one —O—, —S—, —SO—, —CO$_2$—, —CO—, or —CON— moiety.

20. The process of claim 19, wherein the weight ratio of the tertiary amine to the organic acid is between about 50:1 to about 500:1.

21. A process for making solid tertiary amine oxides, said process comprising heating under a nitrogen atmosphere a tertiary amine, iso-propyl alcohol, acetic acid, and aqueous hydrogen peroxide to a temperature between about 50° C. and about 100° C. until at least about 95% of the tertiary amine oxide has reacted, and removing the iso-propyl alcohol and water to yield a free-flowing solid tertiary amine oxide.

22. The process of claim 21, wherein the tertiary amine is at least one tertiary amine selected from the group consisting of didecyl methyl amine, dicocoalkyl methyl amine, ditallowalkyl methyl amine, dieicosyl methyl amine, and didocosanyl methyl amine.

* * * * *